US00PP12713P2

(12) United States Plant Patent
Boekesteijn

(10) Patent No.: US PP12,713 P2
(45) Date of Patent: Jun. 18, 2002

(54) CHRYSANTHEMUM PLANT NAMED 'WHITE YODAVIS'

(75) Inventor: Teun Boekesteijn, De Lies (NL)

(73) Assignee: Yoder Brothers, Inc., Barberton, OH (US)

( * ) Notice: Subject to any disclaimer, the term of this patent is extended or adjusted under 35 U.S.C. 154(b) by 4 days.

(21) Appl. No.: 09/774,360

(22) Filed: Feb. 1, 2001

(51) Int. Cl.[7] ..... A01H 5/00

(52) U.S. Cl. ..... Plt./294

(58) Field of Search ..... Plt./294

(56) References Cited

PUBLICATIONS

UPOV–ROM hits on 'White Yodavis', GTI Jouve Retrieval Software, Plant variety Database, 2001/04.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'White Yodavis', characterized by its upright and uniformly mounded plant habit; dark green foliage; nine-week response time; very freely flowering habit; daisy-type inflorescences that are about 5.2 cm in diameter; white ray florets and bright yellow disc florets; and excellent postproduction longevity with plants maintaining good substance and color for at least three weeks in an interior environment.

1 Drawing Sheet

BACKGROUND OF THE INVENTION

The present Invention relates to a new and distinct cultivar of Chrysanthemum plant, botanically known as *Chrysanthemum×morifolium* and hereinafter referred to by the name 'White Yodavis'.

The new Chrysanthemum is a naturally-occurring whole plant mutation of the Chrysanthemum cultivar Light Davis, disclosed in U.S. Plant Pat. No. 8,293. The new Chrysanthemum was discovered and selected by the Inventor as a single flowering plant within a population of plants of 'Light Davis' in June, 1996 in De Lier, The Netherlands. The selection of this plant was based on its white ray floret color.

Asexual reproduction of the new Chrysanthemum by vegetative tip cuttings was first conducted in De Lier, The Netherlands in August, 1996. Asexual reproduction by cuttings has shown that the unique features of this new Chrysanthemum are stable and reproduced true to type in successive generations.

SUMMARY OF THE INVENTION

The cultivar White Yodavis has not been observed under all possible environmental conditions. The phenotype may vary somewhat with variations in environment such as temperature, daylength, and/or light level, without, however, any variance in genotype.

The following traits have been repeatedly observed and are determined to be the unique charactersitics of 'White Yodavis'. These characteristics in combination distinguish 'White Yodavis' as a new and distinct Chrysanthemum:

1. Upright and uniformly mounded plant habit.
2. Dark green foliage.
3. Typically grown as a natural spray-type.
4. Nine-week response time.
5. Very freely flowering.
6. Daisy-type inflorescences that are about 5.2 cm in diameter.

7. White ray florets and bright yellow disc florets.
8. Excellent postproduction longevity with plants maintaining good substance and color for at least three weeks in an interior environment.

Plants of the new Chrysanthemum can be compared to plants of the parent cultivar Light Davis and the cultivar Davis, disclosed in U.S. Plant Pat. No. 7,325. In side-by-side comparisons conducted in Salinas, Calif., plants of the new Chrysanthemum have white-colored ray florets whereas plants of the cultivar Light Davis have light lavender pink-colored ray florets and plants of the cultivar Davis have lavender pink-colored ray florets.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a top perspective view of a typical flowering plant of 'White Yodavis' grown a natural spray-type.

The photograph at the bottom of the sheet comprises a close-up view of typical inflorescences of 'White Yodavis' grown as a natural spray-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the autumn in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as natural spray-types. Measurements and numerical values represent averages of typical flowering plants.

Botanical classification: *Chrysanthemum×morifolium* cultivar White Yodavis.

Commercial classification: Daisy-type potted Chrysanthemum.

Parentage: Naturally-occurring whole plant mutation of the *Chrysanthemum×morifolium* cultivar Light Davis, disclosed in U.S. Plant Pat. No. 8,293.

Propagation:

*Type.*—Terminal tip cuttings.

*Time to initiate roots.*—About four days at 21° C.

*Time to produce a rooted cutting.*—About ten days at 21° C.

*Root description.*—Fibrous and well-branched.

Plant description:

*Appearance.*—Herbaceous daisy-type potted Chrysanthemum typically grown as a natural spray-type. Stems upright and outwardly spreading giving a uniformly mounded appearance to the plant. Freely branching, about four lateral branches develop after removal of terminal apex (pinching). Moderately vigorous.

*Plant height.*—About 30 cm.

*Plant width.*—About 49 cm.

*Lateral branches.*—Length: About 27 cm. Diameter: About 4 mm. Internode length: About 2 cm. Strength: Strong. Texture: Pubescent. Color: 146A.

*Foliage description.*—Arrangement: Alternate. Quantity of leaves per lateral stem: About 12. Length: About 6.8 cm. Width: About 4.5 cm. Apex: Mucronate to cuspidate. Base: Attenuate. Margin: Palmately lobed, sinuses between lateral lobes mostly parallel. Texture: Upper and lower surfaces with very fine pubescence; veins prominent on lower surface. Color: Young foliage, upper surface: More green than 147A. Young foliage, lower surface: 147B. Mature foliage, upper surface: More green than 147A. Mature foliage, lower surface: 147B. Venation, upper surface: 147A to 147B. Venation, lower surface: 147B. Petiole length: About 2.1 cm. Petiole diameter: About 3 mm. Petiole color: 146B to 146C.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Typically grown as a natural spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 55 days later when grown during the summer and flower about 61 days later when grown during the winter.

*Postproduction longevity.*—Inflorescences maintain good color and substance for at least three weeks in an interior environment.

*Quantity of inflorescences.*—Very freely flowering, about 12 inflorescences develop per lateral stem, or about 48 inflorescences per plant.

*Inflorescence bud:* Height: About 6 mm. Diameter: About 7 mm. Color: 143A.

*Inflorescence size.*—Diameter: About 5.2 cm. Depth (height): About 1.5 cm. Diameter of disc: About 1.4 cm. Receptacle diameter: About 6.5 mm.

*Ray florets.*—Shape: Elongated-oblong. Orientation: Initially upright, then about 70° from vertical. Aspect: Initially concave to somewhat convex. Length: About 2.6 cm. Width: About 9 mm. Corolla tube length: About 3.5 mm. Apex: Rounded, acute or emarginate. Base: Attenuate; short corolla tube. Margin: Entire. Texture: Smooth, glabrous, satiny. Number of ray florets per inflorescence: About 23 arranged in one row. Color: When opening, upper and lower surfaces: 155D. Fully opened, upper and lower surfaces: 155D.

*Disc florets.*—Arrangement: Massed at center of receptacle. Shape: Tubular, elongated. Apex: Five-pointed. Length: About 6 mm. Width: Apex, about 2 mm; base about 1 mm. Number of disc florets per inflorescence: About 127. Color: Immature: 145A to 154A. Mature: Apex: 9A. Mid-section: 154D. Base: 155D.

*Peduncles.*—Length: First peduncle: About 2.3 cm. Fourth peduncle: About 4.4 cm. Seventh peduncle: About 8.1 cm. Diameter: About 2 mm. Angle to vertical: About 50° from vertical. Strength: Moderately strong, flexible. Color: 144A to 146A.

*Reproductive organs.*—Androecium: Present on disc florets only. Anther color: 9A. Pollen amount: Moderate to abundant. Pollen color: 15A. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'White Yodavis', as illustrated and described.

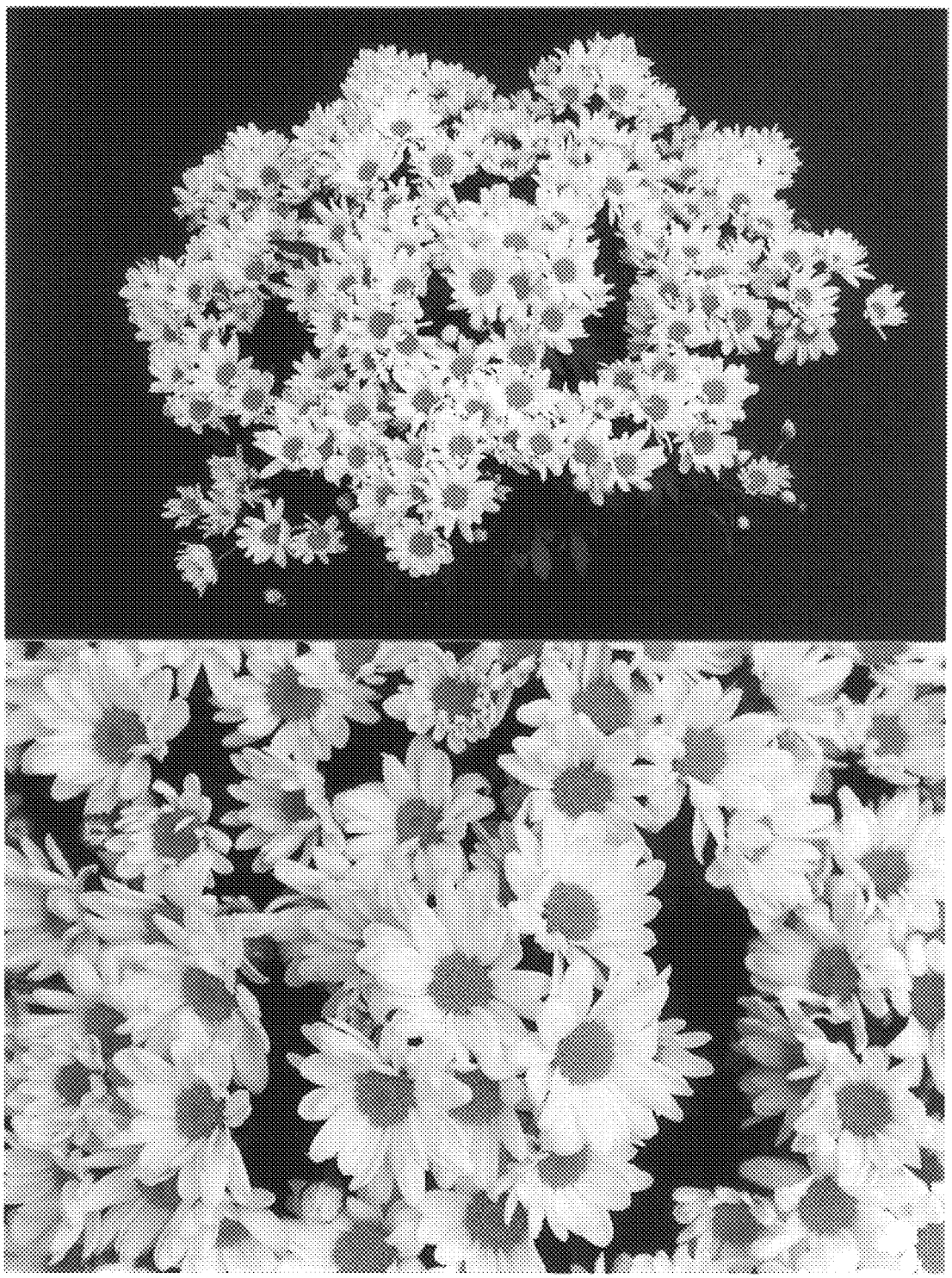

* * * * *